United States Patent [19]

Squire

[11] Patent Number: 4,533,741

[45] Date of Patent: Aug. 6, 1985

[54] 4,5-DICHLORO-2,2,4,5,-TETRAFLUORO-1,3-DIOXOLANE

[75] Inventor: Edward N. Squire, Glen Mills, Pa.

[73] Assignee: E. I. Dupont De Nemours and Company, Wilmington, Del.

[21] Appl. No.: 658,666

[22] Filed: Oct. 9, 1984

Related U.S. Application Data

[62] Division of Ser. No. 421,824, Sep. 23, 1982, Pat. No. 4,485,250.

[51] Int. Cl.$^3$ .............................................. C07D 13/04
[52] U.S. Cl. .................................................... 549/455
[58] Field of Search ......................................... 549/455

[56] References Cited

U.S. PATENT DOCUMENTS

| | | | |
|---|---|---|---|
| 3,475,457 | 10/1969 | Sianesi et al. | 549/455 |
| 3,699,145 | 10/1972 | Sianesi et al. | 549/455 |
| 3,734,862 | 5/1973 | Maulding | 549/455 |
| 3,749,791 | 7/1973 | Terrell et al. | 549/455 |
| 3,812,261 | 5/1974 | Hartmann | 549/455 |
| 3,865,845 | 2/1975 | Resnick | 549/455 |
| 4,017,519 | 4/1977 | Moore et al. | 549/455 |
| 4,287,124 | 9/1981 | Siegemund et al. | 549/455 |

*Primary Examiner*—Harry Wong, Jr.

[57] ABSTRACT

Perfluoro-1,3-dioxole, prepared by dechlorinating 4,5-dichloro-2,2,4,5-tetrafluoro-1,3-dioxolane with magnesium, is a useful monomer, which polymerizes to either amorphous or liquid homopolymers and copolymerizes with tetrafluoroethylene as well as with other monomers to both crystalline and amorphous copolymers having one or more such comonomers incorporated therein. Amorphous homopolymers and copolymers of perfluoro-1,3-dioxole are useful in such applications as glazing for reactors for hydrogen fluoride reactions. Amorphous homopolymers and amorphous or crystalline copolymers form self-supporting films and can be used for coatings and linings which are inert to most chemicals and are stain and weather resistant and as dielectrics for electrical and electronic equipment. Liquid homopolymers can be used as hydraulic fluids and heat exchange media.

1 Claim, No Drawings

4,5-DICHLORO-2,2,4,5,-TETRAFLUORO-1,3-DIOXOLANE

CROSS-REFERENCE TO RELATED APPLICATION

This a divisional of my copending application Ser. No. 421,824, filed Sept. 23, 1982, now U.S. Pat. No. 4,485,250.

BACKGROUND OF THE INVENTION

This invention is directed to perfluoro-1,3-dioxole (sometimes referred to hereafter as perfluorodioxole or PD), its preparation, and its polymerization products.

While perfluoro(2,2-dimethyl-1,3-1,3-dioxole) and its polymers are known from U.S. Pat. Nos. 3,865,845 and 3,978,030 to Resnick, the simplest member of the family, PD, shown in Formula (1) below, has never been reported:

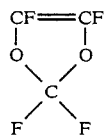

SUMMARY OF THE INVENTION

According to this invention, there are now provided: perfluoro-1,3-dioxole, homopolymers and copolymers of perfluoro-1,3-dioxole, and processes for making perfluoro-1,3-dioxole.

DETAILED DESCRIPTION OF THE INVENTION

PD can be conveniently made in four steps from ethylene carbonate, as shown in the following reaction sequence:

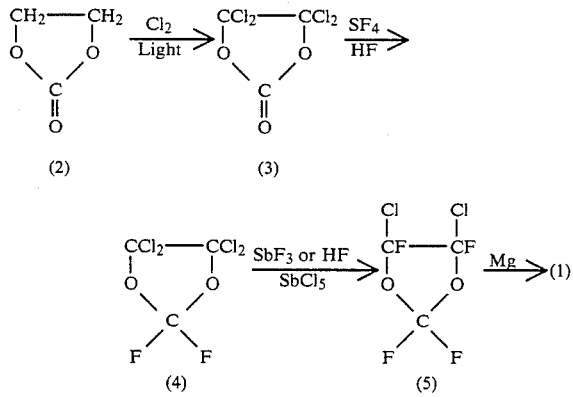

Thus, ethylene carbonate (2) is chlorinated in the presence of light to tetrachloroethylene carbonate (3), which is fluorinated with sulfur tetrafluoride in the presence of hydrogen fluoride to 4,4,5,5-tetrachloro-2,2-difluoro-1,3-dioxolane (4). This compound reacts with either antimony trifluoride or hydrogen fluoride in the presence of antimony pentachloride to yield 4,5-dichloro-2,2,4,5-tetrafluoro-1,3-dioxolane (5), which is dechlorinated with magnesium to PD (1). This last step is preferably carried out in the presence of mercuric chloride and iodine.

Another synthetic route starts with 1,3-dioxolane (6), which is perchlorinated to hexachloro-1,3-dioxolane (7), then fluorinated either with antimony trifluoride or with hydrogen fluoride in the presence of SbCl$_5$ to (5), which then is dechlorinated as before. This reaction sequence is shown below:

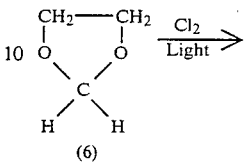

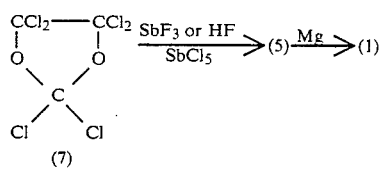

Perfluorodioxole is a gas which boils at about 0° C. Since its toxicity is unknown, it should be treated as a potential health hazard. In addition, it is flammable at volume concentrations of about 5–40% in air.

PD forms with tetrafluoroethylene (TFE) tough, crystalline copolymers, suitable as dielectrics in electrical and electronic equipment. The PD content in these copolymers ranges from less than 1 to about 12 mole percent, as determined by nuclear magnetic resonance (NMR) spectroscopy. As the PD content increases beyond approximately 12 mole percent, its copolymers with TFE become amorphous. They can be used in coatings and finishes resistant to chemicals, stains, and weather.

It sometimes is advantageous to copolymerize PD with TFE and a third ethylenically unsaturated monomer. Such third monomer may be among others an olefin, such as ethylene, propylene, isobutylene, or butene-1; a fluoroolefin, such as vinylidene fluoride, hexafluoropropylene, or chlorotrifluoroethylene; or a monomer carrying a functional group, such as a perfluoro(alkyl vinyl ether), methyl 3-[1-[difluoro[(trifluoroethenyl)oxy]methyl]-1,2,2,2-tetrafluoroethoxy]-2,2,3,3-tetrafluoro-propanoate, and 2-[1-[difluoro[(trifluoroethenyl)oxy]methyl]-1,2,2,2-tetrafluoroethoxy]-1,1,2,2-tetrafluoroethanesulfonyl fluoride.

The presence of a third monomer in the copolymer may lower the copolymer cost, for example when either PD of TFE is replaced in part by an olefin. It may change the copolymer's properties, for example, from crystalline to amorphous or from non-elastomeric to elastomeric. Finally, the third monomer permits the introduction of functional groups, for example fluorosulfonyl or methoxycarbonyl.

Depending on the specific third monomer as well as on the relative proportions of all comonomers, the terpolymer may or may not be crystalline. There is no absolute numerical line of demarcation which would permit to predict the crystalline character of a terpolymer from the relative proportions of monomers. As a general guideline, the crystalline character of a terpolymer increases as the proportion of TFE increases. Moreover, it is possible to have amorphous terpolymers in which the proportion of PD is considerably less than 12 mole % as well as crystalline terpolymers in which it is well above 12 mole %.

Terpolymers of PD with TFE and another monomer will thus have a broad range of applications in coatings, in high performance elastomers and plastics and as intermediates to polymers having other functional groups.

Dipolymers of PD with monomers other than TFE also are possible, although not all ethylenically unsaturated monomers will copolymerize with PD in the absence of a third monomer. For example, α-olefins will not form dipolymers with PD, but fluoroolefins and monomers carrying a functional group, such as those recited above in connection with terpolymers of PD will copolymerize with PD to form dipolymers. The preferred such comonomer, both in PD dipolymers and in terpolymers with PD and TFE is vinylidene fluoride.

While copolymers of PD with TFE and another ethylenically unsaturated monomer are the most likely of all terpolymers to find industrial applications, terpolymers of PD with other ethylenically unsaturated monomers also can be made, and this invention is not limited to the use of any specific type or number of monomers that can be copolymerized with PD. Obviously, for practical reasons one would not wish to run the polymerization with an excessive number of monomers, but that is only a practical limitation, rather than a limitation of the invention.

The last step in the preparation of PD, dechlorination of 4,5-dichloro-2,2,4,5-tetrafluoro-1,3-dioxolane (5), is preferably carried out in a tetrahydrofuran solution. In spite of the large difference between the boiling points of PD and tetrahydrofuran, which boils at 65°–66° C., a small amount of tetrahydrofuran (about 1% or less) is usually present in distilled PD. When PD is further purified, for example, by aqueous extraction followed by distillation on a spinning band column, it has a tendency to polymerize spontaneously at temperatures of about room temperature to about −5° C. Highly purified PD polymerizes spontaneously even in a dry ice chest. PD homopolymers are amorphous solids. When made in the presence of small amounts of tetrahydrofuran, for example, 2% of the weight of PD or less, they have a glass transition temperature, Tg, within the range of about 84°–92° C., while the homopolymers made in the absence of tetrahydrofuran have two Tg's, at about 172°–179° C. and 212° C.

Amorphous homopolymers and copolymers of PD are useful in glazing reactors for hydrogen fluoride reactions. Amorphous homopolymers and amorphous or crystalline copolymers of PD form self-supporting films and can be used for coatings and linings which are inert to most chemicals and are stain and weather resistant and as dielectrics for electrical and electronic equipment.

When allowed to stand at room temperature with modest amounts of tetrahydrofuran, for example, 10–100% of the weight of PD, PD forms low molecular weight polymers, which are greases or liquids. They are suitable in such applications as hydraulic fluids, lubricants, and heat exchange media.

This invention is now illustrated by the following examples of certain representative embodiments thereof, where all parts, proportions, and percentages are by weight unless otherwise indicated.

Synthesis of PD (a) Tetrachloroethylene Carbonate (3)

A 1000 mL creased flask equipped with a stirrer, a thermometer, a gas inlet tube, and a water condenser topped by a dry ice condenser, was charged with 352.4 g (4 moles) of melted ethylene carbonate. The apparatus was purged with nitrogen while stirring and heating to 50° C. After turning off the nitrogen, chlorine was introduced at a rapid rate and, when the solution turned yellow, a sunlamp was lit. The flow of chlorine and the intensity of the light were adjusted so that the solution remained yellow and the temperature did not exceed 80° C. during the first few hours of chlorination. Later, the temperature could be increased to 100°–120° C.

Periodically, a sample of the reaction mixture was analyzed by gas chromatography. The chlorination was continued until gas chromatography showed that incompletely chlorinated intermediates were absent in the product. The product was distilled at a reduced pressure on a water aspirator. After the removal of chlorine and hydrogen chloride, the distillation could be continued using a high vacuum pump.

Tetrachloroethylene carbonate boils at 46° C. at about 666 Pa. The pure product was recovered in yields as high as 94%.

(b) 4,4,5,5-Tetrachloro-2,2-difluoro-1,3-dioxolane (4)

A 360 mL "Hastelloy" C. shaker tube was charged with 113 g (0.5 mole) of tetrachloroethylene carbonate, sealed under nitrogen, cooled in a dry ice acetone mixture, evacuated, flushed with nitrogen, reevacuated and charged with 18 g (0.9 mole) of hydrogen fluoride and 194 g (1.8 mole) of sulfur tetrafluoride. The tube was agitated for 10 hours at 200° C. The tube was next chilled in an ice-water bath and then slowly vented to remove the excess $SF_4$ and HF. The product was dumped from the tube into wet ice and allowed to stand a day. The organic phase was separated from the aqueous phase in a polyethylene separatory funnel, then stirred with a 30% aqueous solution of potassium carbonate to neutralize free acid. The product was dried over potassium carbonate and distilled at a reduced pressure. It boils at 126° C. at atmospheric pressure. The best yield of 4,4,5,5-tetrachloro-2,2,-difluoro-1,3-dioxolane was 73%. Infrared and nuclear magnetic resonance (NMR) spectra support the chemical structure (4) of this dioxolane.

(c) 4,5-Dichloro-2,2,4,5-tetrafluoro-1,3-dioxolane (5)

A 500 mL, 3-neck, borosilicate, round bottom flask equipped with a mechanical stirrer, water condenser topped by a small dry ice trap, a nitrogen bubbler, and a thermometer was charged with 193 g (1.08 moles) of $SbF_3$, 124 g (0.415 mole) of $SbCl_5$, and 99 g (0.4 mole) of 4,4,5,5-tetrachloro-2,2-difluoro-1,3-dioxolane. The stirred reactants were heated to reflux with vigorous agitation for 7 hours.

The flask contents were distilled directly from the residual solid antimony salts at reduced pressures down to about 130 Pa with slight heating of the flask at the end of the distillation. The distillate was then extracted with two 10 mL portions of 21% aqueous hydrochloric acid after which it was distilled from solid $K_2CO_3$ or molecular sieves.

The best yield was over 90%, but yields were erratic. The pure product boils at 49° C. at atmospheric pressure. Infrared and NMR analyses support the chemical structure of this dioxolane.

(d) Perfluorodioxole (PD) (1)

A 300 mL distilling flask with two side arms, equipped with a magnetic stirrer, a thermometer, a syringe needle entrance, and a distilling column topped by a water condenser and a dry ice condenser arrangement leading to a stainless steel cylinder collector in series with a nitrogen bubbler, was charged with 7.3 g (0.3 mole) of magnesium turnings, 0.2 g (0.00074 mole) of mercuric chloride, 0.2 g (0.00079 mole) of iodine, and 80 mL (1 mole) of tetrahydrofuran.

The mixture was heated to about 60°–65° C., and the color of the mixture changed from red to gray. 4,5-Dichloro-2,2,4,5-tetrafluoro-1,3-dioxolane (21.5 g, 0.1 mole) was pumped into the flask through a syringe needle at the rate of 0.24 mL/min. After the introduction of about 4 mL, the mixture turned dark, and the reaction heat was sufficient to cause vigorous refluxing in the dry ice condenser. The product, perfluorodioxole, was distilled from the mixture at about $-5°$ to $+5°$ C. (head temperature) and collected in the stainless steel cylinder.

Crude PD can be purified by slowly passing it through a cold 2% aqueous solution of potassium carbonate and through cold water to remove tetrahydrofuran and other water-soluble impurities, then collecting the purified PD in a glass container maintained at a dry ice temperature. PD is best dissolved in 1,1,2-trichloro-1,2,2-trifluoroethane and kept in solution at a low temperature until needed. The solutions can be used in polymerization reactions.

Alternative synthesis of perfluorodioxole

(a) Hexachloro-1,3-dioxolane (7)

A 300 mL creased, 3-neck borosilicate flask equipped with a thermometer, a gas inlet tube, and a water condenser topped by a dry ice condenser leading to a drying tower and and then to a water scrubber was charged with 37 g (0.5 mole) of 1,3-dioxolane and 200 g (1.07 mole) of 1,1,2-trichloro-1,2,2-trifluoroethane. After purging the system with nitrogen, chlorine gas was introduced into the flask at 19° C. The solution was then irradiated with a mercury vapor ultraviolet lamp. The rate of chlorine flow was such that the solution was yellow at all times and the illuminaton intensity was regulated so that the temperature did not rise above 35° C. during the first few hours of chlorination. The chlorination was continued for 21 hours while the maximum temperature was maintained between 44° and 50° C. The 1,1,2-trichloro-1,2,2-trifluoroethane and small amounts of chlorine and hydrogen chloride were distilled off at the pressure of a water aspirator. The crude product was extracted with distilled water containing a small amount of tetrahydrofuran, then again with water, finally stirred with solid potassium carbonate. The product was then distilled at a pressure of about 133 Pa and a temperature of 29° C. to yield 52.8 g of (7); the infrared absorbance spectrum was consistent with the chemical structure of this dioxolane.

(b) 4,5-Dichloro-2,2,4,5-tetrafluoro-1,3-dioxolane (5)

First Alternative

A 250 mL, 3 neck, round bottom flask equipped with a mechanical stirrer, thermometer and a reflux condenser leading to a dry ice trap under 0.1 MPa of nitrogen was charged with 107.3 g (0.6 mole) of antimony trifluoride and 69.4 g (0.232 mole) of antimony pentachloride. The mixture was stirred and hexachloro-1,3-dioxolane, 28 g (0.1 mole), was introduced into the flask by syringe; the flask was heated to 55° C., but the temperature gradually dropped to 49° C. Heating was continued for 7 hours. The product was distilled through a short Vigreux column at room temperature and pressures gradually decreasing to about 260 Pa and was collected in a receiver cooled with dry ice. The distillate was extracted twice with 5 mL portions of 21% aqueous hydrochloric acid and redistilled at a reduced pressure from solid potassium carbonate to give 6.9 g of a clear, colorless, liquid product. Its infrared and NMR spectra were consistent with the chemical structure of (5).

Second Alternative

A 330 mL "Hastelloy" C shaker tube was charged under anhydrous conditions with 81.3 g (0.33 mole) of 4,4,5,5-tetrachloro-2,2-difluoro-1,3-dioxolane, 9.0 g (0.03 mole) of $SbCl_5$, and 20 g (1 mole) of hydrogen fluoride. The tube was heated to 70° C. and mechanically shaken for 7 hours. After cooling to room temperature the product was washed with distilled water, then with an aqueous 10% solution of sodium carbonate, and finally distilled to yield 19.5 g of a clear, colorless liquid product. Gas chromatography showed that 67% of this product was the desired 4,5-dichloro-2,2,4,5-tetrafluoro-1,3-dioxolane (5), while about 25% was 4,4,5-trichloro-2,2,5-trifluoro-1,3-dioxolane, and about 8% of other materials, most of them higher boiling. The dioxolane (5), which boils at 46° C. at atmospheric pressure, can be separated by fractional distillation from the trichlorotrifluorodioxolane (b.p. 83°–84° C.) and the other contaminants, which also include some unchanged starting dioxolane (4).

(c) Perfluoro-1,3-dioxole (1)

The same method of dechlorination is used as described above under "Synthesis of PD", step (d).

Amorphous Copolymers of PD with TFE

A 110 mL stainless steel shaker tube was charged with 120 g (0.64 mole) of 1,1,2-trichloro-1,2,2-trifluoroethane, 7.0 g (0.049 mole) of PD, 0.015 g (0.000046 mole) of perfluoropropionyl peroxide, 0.08 mL of cyclohexane, and 3 g (0.03 mole) of TFE. The tube was agitated one hour at 50° C. and one hour at 55° C. After cooling and discharging the contents, the unchanged monomers and the 1,1,2-trichloro-1,2,2-trifluoroethane were distilled off, and the polymer remaining in the tube was dried in a vacuum oven at 110° C. The yield was 4.7 g of colorless material (a 47% conversion), which was found by NMR spectroscopy to be a copolymer of 81.7 mole % of PD and 18.3 mole % of TFE. It had a Tg of 135° C.; its 230° C. melt viscosity was $1.42 \times 10^3$ Pa.s.

Additional amorphous copolymers of PD with TFE were obtained by the same technique from different proportions of the starting monomers and at different conversions. The following table summarizes those runs:

TABLE 1

| Monomer | | | Polymer | | | Melt |
|---|---|---|---|---|---|---|
| PD Mole % | TFE Mole % | Conversion % | PD Mole % | TFE Mole % | Tg °C. | Viscosity (Pa·s at 230° C.) |
| 100 | 0 | 82 | 100 | 0 | 173,212 | — |
| 61.8 | 38.2 | 47 | 81.7 | 18.3 | 135 | $1.42 \times 10^3$ |
| 55.0 | 45.0 | 56 | 75 | 25 | 124 | $5.8 \times 10^3$ |
| 62.7 | 37.3 | 60 | 76.1 | 23.9 | 125 | $2.68 \times 10^4$ |
| 64.4 | 35.6 | 65 | — | — | 131 | $3.0 \times 10^4$ |
| 59.0 | 41.0 | 46 | — | — | 130 | $1.4 \times 10^3$ |

The following physical properties were determined at 23° C./50% relative humidity for the 76.1/23.9 PD/TFE copolymer of Table 1:

TABLE 2

| | |
|---|---|
| Modulus (MPa) From stress/strain plot | 1703 |
| Stress (MPa) ASTM D1708 | |
| Yield | 43.4 |
| Maximum | 43.4 |
| Break | 43.4 |
| Strain (%) ASTM D1708 | |
| Yield | 5.9 |
| Break | 19.9 |

The modulus and stress values for these amorphous perfluorodioxole copolymers are higher than reported in the literature for any other perfluorocarbon resin. In addition, these copolymers have an outstanding cut through resistance and low creep characteristics for perfluorocarbon resins, which makes them useful in electrical insulation and in various mechanical parts.

Crystalline Copolymers of PD with TFE

A 110 mL stainless steel shaker tube was charged with 110 g (0.59 mole) of 1,1,2-trichloro-1,2,2-trifluoroethane, 1.5 g (0.01 mole) of PD, 0.03 g (0.000075 mole) of bis(4-t-butylcyclohexyl) peroxydicarbonate, and 10 g (0.1 mole) of TFE. The tube was agitated for 3 hours at 55°–65° C. The unpolymerized monomers were vented, and the polymer suspension was transferred to a 355 mL stainless steel shaker tube, which was charged with 0.2 g of water and pressurized to 1.1 MPa with a mixture of 25 vol. % of fluorine and 75 vol. % of nitrogen. The tube was agitated 8 hours at 200° C. The clear solvent was decanted after cooling. The residual polymer was dried. It weighed 6.2 g. The above fluorination step was necessary to break up the difficultly filterable suspension of the polymer in the solvent. The polymer had a melting point of 309° C., as determined by differential thermal analysis, and a melt viscosity of $6.8 \times 10^3$ Pa.s at 380° C.

Other crystalline copolymers of PD with TFE were prepared by this technique. Their melting points were in the range of 306°–326° C. In all cases the amount of PD incorporated into the copolymer was less than about 12 mole %. When the amount of PD was increased beyond this value, the copolymers were either substantially or completely amorphous.

The copolymer melting at 309° C. was pressed at 380° C. into a thin film. The tensile properties of this film were compared with those of a film made from a commercial resin, "Teflon" PFA 350, which is a fluorocarbon copolymer having perfluoroalkoxy side chains. The results are shown in the following table:

TABLE 3

| | Polymer of | |
|---|---|---|
| | TFE/PD | "Teflon" PFA 350 |
| Melting point (°C.) | 309 | 306 |
| Stress (MPa) | | |
| Yield | 15.2 | 15.2 |
| Maximum | 23.4 | 23.4 |
| Break | 23.4 | 23.4 |
| Strain (%) | | |
| Yield | 4.9 | 20.7 |
| Break | 210.4 | 326.3 |

As can be seen, the TFE/PD copolymer of this invention has the same tensile strength as the commercial resin but lower elongation.

An Elastomeric Terpolymer of PD, Vinylidene fluoride and TFE

A 110 mL stainless steel shaker tube is charged with 100 g of 1,1,2-trichlorotrifluoroethane, 2.0 g of PD, 0.02 g of bis(4-t-butylcyclohexyl) peroxydicarbonate, 6.0 g of vinylidene fluoride and 5.0 g of TFE. The polymerization is carried out under autogeneous pressure for 3 hours at 55°–65° C. After cooling, the tube contents are transferred to a still; after distilling off the unchanged monomers and trichlorotrifluoroethane a white, solid polymer, 5.1 g, is obtained. A portion of the polymer is compression formed at 230° C. to give a thin, tough, elastomeric, clear, self supporting film.

A Crystalline Terpolymer of PD, Ethylene and TFE

A 110 mL stainless steel shaker tube is charged with 100 g of 1,1,2-trichlorotrifluoroethane, 1.0 g of PD, 0.03 g of bis(4-t-butylcyclohexyl) peroxydicarbonate, 1.0 g of ethylene and 12 g of TFE. The agitated tube is heated at 55°–65° C. for three hours under autogenous pressure. Following the polymerization the trichlorotrifluoroethane and unchanged monomers are distilled off leaving 9.8 g of a white crystalline solid. This polymer is compression formed at 350° C. into thin, tough, plastic films.

An amorphous terpolymer of PD, 2-[1-[difluoro[(trifluoroethenyl)oxy]methyl]-1,2,2,2-tetrafluoroethoxy]-1,1,2,2,-tetrafluoroethanesulfonyl fluoride, and TFE A 110 mL stainless steel shaker tube is charged with 100 g of 1,1,2-trichlorotrifluoroethane, 0.03 g of bis(4-t-butylcyclohexyl)peroxydicarbonate, 4 g of PD, 10 g of TFE, and 1 g of 2-[1[difluoro[(trifluoroethenyl)oxy]methyl]-1,2,2,2-tetrafluoroethoxy]-1,1,2,2-tetrafluoroethanesulfonyl fluoride. The tube is agitated and the polymerization is carried out at 55°–65° C. under autogenous pressure for three hours. After distilling off the unchanged monomers and trichlorotrifluoroethane, there is obtained 10.2 g of a white, granular, solid polymer. This polymer is compression formed at 230° C. into a thin, tough, transparent film. The polymer has no crystalline melting point and thus is amorphous.

Homopolymer of PD (a) A 110 mL stainless steel shaker tube was charged with 120 g of 1,1,2-trichloro-1,2,2-trifluoroethane, 0.02 g of perfluoropropionyl peroxide, and 6.2 g of PD (purified by water scrubbing) and heated for 3 hours with agitation at 50°–55° C. After cooling to room temperature, the tube was discharged; the solvent was distilled off, and the solid was dried at 110° C. in a vacuum oven to give 5.1 g of a homopolymer which exhibited Tg's at 173° C. and 212° C. The absence of a crystalline melting point and X-ray analysis demonstrated that the polymer was amorphous. The PD homopolymer was compression formed at 340° C. into a film which had the following tensile characteristics, determined at 23° C./50% relative humidity:

TABLE 4

| | |
|---|---|
| Modulus (MPa) | 1373 |
| From stress/strain plot | |
| Stress (MPa) ASTM D1708 | |
| Yield | 49 |
| Maximum | 49 |
| Break | 49 |
| Strain (%) | 4.9 |
| Break | |

(b) In the homopolymerizaton of PD which was distilled but not water-scrubbed (and thus contained a minor amount of tetrahydrofuran), the solid polymer formed under similar conditions had low Tg's, within the range of 84°–92° C. It was determined by infrared analysis that a small amount of THF was incorporated in the polymer chain.

(c) Small amounts of tetrahydrofuran (say, 10 to 100 vol. % of PD) inhibit homopolymerization of PD to solid homopolymer during storage. However, low molecular weight polymers or oligomers of PD formed spontaneously on standing at room temperature. These were liquids from which unpolymerized PD could be readily separated by distillation. These low molecular weight polymers were readily identifiable by their characteristic infrared spectra, which were consistent with a chemical structure containing perfluorodioxole units as well as tetrahydrofuran units.

Utility of PD/TFE Copolymer as a Coating

A mild steel wire was immersed in concentrated hydrochloric acid; chemical attack on the wire was evident in less than 10 seconds by the formation of bubbles on the wire. The wire was removed from the acid, washed with water and dried. A solution of 1 g of a 125° C. Tg TFE/PD copolymer in 20 mL "Fluorinert Electronic Liquid" FC75 (a 3M product) was made by shaking the polymer in the liquid. The wire was then dip-coated with this solution and dried at 90° C. in a vacuum oven. The coated wire when immersed in concentrated hydrochloric acid for several minutes was not attacked.

A section of soft wood was similarly coated and dried. Immersion of this in water for several minutes failed to show any water absorbance. However, uncoated wood absorbed water in less than 10 seconds.

I claim:

1. 4,5-Dichloro-2,2,4,5-tetrafluoro-1,3-dioxolane.

* * * * *